US00PP27628P2

(12) United States Plant Patent
Zaiger et al.

(10) Patent No.: US PP27,628 P2
(45) Date of Patent: Jan. 31, 2017

(54) NECTARINE TREE NAMED 'LEILA'

(50) Latin Name: ***Prunus persica* var. *nucipersica***
Varietal Denomination: Leila

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 14/757,127

(22) Filed: Nov. 24, 2015

(51) Int. Cl.
*A01H 5/08* (2006.01)

(52) U.S. Cl.
USPC ..... Plt./190

(58) Field of Classification Search
USPC ..... Plt./190
CPC ..... A01H 5/0856
See application file for complete search history.

*Primary Examiner* — Kent L Bell

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth habit.
2. Regular and productive bearer of large size, yellow flesh fruit.
3. Fruit with good flavor and eating quality.
4. Fruit with an attractive dark red skin color.
5. Fruit with good handling and shipping qualities.

1 Drawing Sheet

Botanical designation: *Prunus persica* var. *nucipersica*.
Variety denomination: 'Leila'.

BACKGROUND OF THE VARIETY:

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine trees, which are known to us, and mentioned herein, 'Zee Fire' Nectarine (U.S. Plant Pat. No. 13,501) and our proprietary non-patented nectarine seedling selections with the field identification numbers '42ZN84' and '9ZL640'.

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was developed by us in our experimental orchard located near Modesto, Calif. from open pollinated seed collected from our proprietary non-patented nectarine seedling selection with the field identification number '42ZN84'. The seed parent (42ZN84) originated as an open pollinated seedling selection from our proprietary non-patented nectarine seedling selection '9ZL640'. A large group of these open pollinated seedlings were budded onto older established trees of 'Nemaguard' Rootstock (non-patented) to enhance earlier fruit production. Under close and careful observation the present budded seedling exhibited desirable fruit and tree characteristics and was selected in 2012 for additional asexual propagation and commercialization.

ASEXUAL REPRODUCTION OF THE VARIETY

In 2012 asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of nectarine tree (*Prunus persica* var. *nucipersica*) is of large size, vigorous, upright growth and a regular and productive bearer of large size, yellow flesh, clingstone fruit ripening in the early maturity season. The fruit is further characterized by having an attractive dark red skin color, good flavor with good handling and shipping qualities. In comparison to its proprietary non-patented nectarine seed parent '42ZN84' the fruit of the new variety is approximately 8 days earlier in maturity. In comparison to the commercial variety 'Zee Fire' Nectarine (U.S. Plant Pat. No. 13,501) the fruit of the new variety is larger in size and the flowers have an average of 15 petals compared to 5.

DESCRIPTION OF THE PHOTOGRAPH

The accompanying color photographic illustration shows typical specimens of the foliage and fruit of the present new nectarine variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 4 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 4 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with type and fertility of soil, climatic conditions and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 3 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 350 hours at or below 45° F.

Trunk:

*Size*.—Large, average circumference 40.6 cm at 25.4 cm above ground on a 4 year old tree.

*Stocky*.—Medium stocky.

*Texture*.—Medium shaggy, roughness increases with age.

*Color*.—Varies from 5Y 4/2 to 7.5Y 4/2.

Branches:

*Size*.—Medium. Average circumference 5.8 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 41 in a 25.8 square cm area. Average length 3.0 mm. Average width 1.6 mm. Color varies from 7.5YR 5/10 to 7.5YR 5/8.

*Color*.—New growth varies from 2.5GY 6/8 to 2.5GY 6/6. Mature growth varies from 7.5YR 3/6 to 7.5YR 3/4, varies with age of growth.

Leaves:

*Size*.—Medium to large. Average length 122.0 mm. Average width 32.9 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Medium. Average length 9.5 mm. Average width 1.4 mm. Longitudinally grooved. Surface — glabrous. Color varies from 2.5GY 5/6 to 2.5GY 6/6.

*Glands*.—Type — reniform. Size — medium to large. Average length 1.4 mm. Average diameter 1.0 mm. Number varies from 1 to 3, average number 2. Located primarily on the base of the leaf blade and upper portion of the petiole. Color varies from 10YR 4/6 to 10YR 5/6.

*Stipules*.—Average number 2. Average length 7.0 mm. Edges — pectinate. Color varies from 2.5GY 6/6 to 2.5GY 5/6.

*Color*.—Upper surface varies from 5GY 4/4 to 2.5GY 3/4. Lower surface varies from 5GY 4/4 to 2.5GY 5/4. Midvein color varies from 2.5GY 8/6 to 2.5GY 7/8.

Flower buds:

*Size*.—Large. Average length 18.5 mm. Average diameter 15.5 mm.

*Hardiness*.—Hardy with respect to California winters.

*Density*.—Medium dense.

*Form*.—Conical, becoming elongated just before opening.

*Pedicel*.—Medium. Average length 7.8 mm. Average width 1.5 mm. Surface — glabrous. Color varies from 5GY 8/8 to 5GY 7/10.

*Color*.—Varies from 5RP 8/6 to 5RP 7/10.

Flowers:

*Blooming period*.—Date of First Bloom Feb. 1, 2015. Date of Petal Fall Feb. 11, 2015, varies slightly with climatic conditions.

*Size*.—Large, showy, double flower. Average length 15.8 mm. Average diameter 41.2 mm.

*Petals*.—Number varies from 10 to 18, average number 15. Size — large. Average length 21.2 mm. Average width 17.4 mm. Form — globose to ovate. Margin — sinuate. Arrangement — overlapping. Petal apex — rounded to ovate. Petal base — truncate. Color varies from 5RP 8/4 to 5RP 7/8, varies with age of flower. Both upper and lower surfaces glabrous.

*Sepals*.—Number varies from 8 to 15, average number 12. Size — medium to large. Average length 7.0 mm. Average width 6.3 mm. Shape — triangular. Apex rounded to triangular. Margin — entire. Color — upper surface varies from 5GY 4/6 to 7.5GY 5/6.

Lower surface varies from 2.5R 2/8 to 5R 2/8. Surface — upper surface glabrous, lower surface pubescent.

*Stamens*.—Average number per flower 75. On average, the stamens are below the height of the petals. Average filament length 11.0 mm. Filament color varies from N 9.5/(white) to 5RP 9/2. Anther color varies from 7.5R 5/12 to 5Y 8.5/10.

*Pollen*.—Self fertile. Color varies from 5Y 8/12 to 5Y 7/12.

*Pistil*.—Number — normally one. Average length 20.8 mm. Position of stigma an average of 4.8 mm above anthers. Surface — glabrous. Color varies from 5Y 8.5/4 to 5Y 9/6.

*Fragrance*.—Wanting.

*Color*.—Varies from 5RP 8/6 to 5RP 7/10.

*Pedicel*.—Average length 8.6 mm. Average width 1.6 mm. Color varies from 5GY 8/6 to 5GY 6/10.

*Number flowers per flower bud*.—Normally one.

Fruit:

*Maturity when described*.—Firm ripe and ready for consumption.

*Date of first picking*.—May 20, 2015.

*Date of last picking*.—May 30, 2015, varies slightly with climatic conditions.

*Size*.—Large. Average diameter axially 71.0 mm. Average transversely in suture plane 74.0 mm. Average weight 224.4 grams, varies slightly with fertility of soil, amount of thinning and climatic conditions.

*Form*.—Globose to slightly elongated.

*Suture*.—Slightly lipped, extends from base to apex.

*Ventral surface*.—Slightly lipped.

*Apex*.—Slightly retuse.

*Base*.—Flat to slightly retuse.

*Stem cavity*.—Rounded to slightly elongated in suture plane. Average depth 8.7 mm. Average diameter 9.5 mm.

Stem:

*Size*.—Medium to large. Average length 10.8 mm. Average diameter 3.6 mm.

*Color*.—Varies from 2.5GY 6/8 to 2.5GY 8/8.

Flesh:

*Ripens*.—Evenly to slightly earlier at the apex.

*Texture*.—Firm, meaty, crisp.

*Fibers*.—Few, small, tender.

*Firmness*.—Good, comparable to other commercial nectarine varieties.

*Aroma*.—Slight.

*Amydgalin*.—Undetected.

*Eating quality*.—Good.

*Flavor*.—Good, with a good balance between acid and sugar.

*Juice*.—Moderate amount, enhances flavor.

*Acidity*.—Not available.

*Brix*.—Average Brix 14.0°, varies slightly with amount of fruit per tree and climatic conditions.

*Color*.—Varies from 2.5Y 8.5/12 to 5Y 8/10.

*Pit cavity*.—Average length 37.0 mm. Average width 32.2 mm. Average depth 13.1 mm. Color varies from 5Y 8/6 to 5Y 8/10.

Skin:

*Thickness*.—Medium.

*Surface*.—Smooth to slightly waffled.

*Pubescence*.—None.

*Tendency to crack*.—None.

*Color*.—Ground color varies from 5Y 8/8 to 5Y 8/10. Overspread with 7.5R 3/10 to 10R 3/10.

*Tenacity*.—Tenacious to the flesh.

*Astringency*.—Undetected.

Stone:

*Type*.—Clingstone, strong adherence to flesh.

*Size*.—Large. Average length 36.0 mm. Average width 31.2 mm. Average thickness 24.1 mm.

*Form*.—Obovoid.

*Base*.—Flat.

*Apex*.—Pointed. Average length 0.9 mm.

*Surface*.—Pitted throughout, pits vary from round to elongated.

*Sides*.—Unequal, one side extending further from suture plane.

*Ridges*.—Relatively smooth, extending from base to apex.

*Tendency to split*.—Very slight to none.

*Color*.—Varies from 10YR 7/6 to 10YR 6/8 when dry.

Kernel:

*Size*.—Large. Average length 17.8 mm. Average width 13.2 mm. Average depth 7.4 mm.

*Form*.—Ovoid.

*Viability*.—Partially viable, incomplete development in most embryos.

*Skin color*.—Varies from 5Y 9/6 to 7.5Y 9/4.

Use: Dessert.

*Market*.—Local and long distance.

Keeping quality: Good, held firm in cold storage 2 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

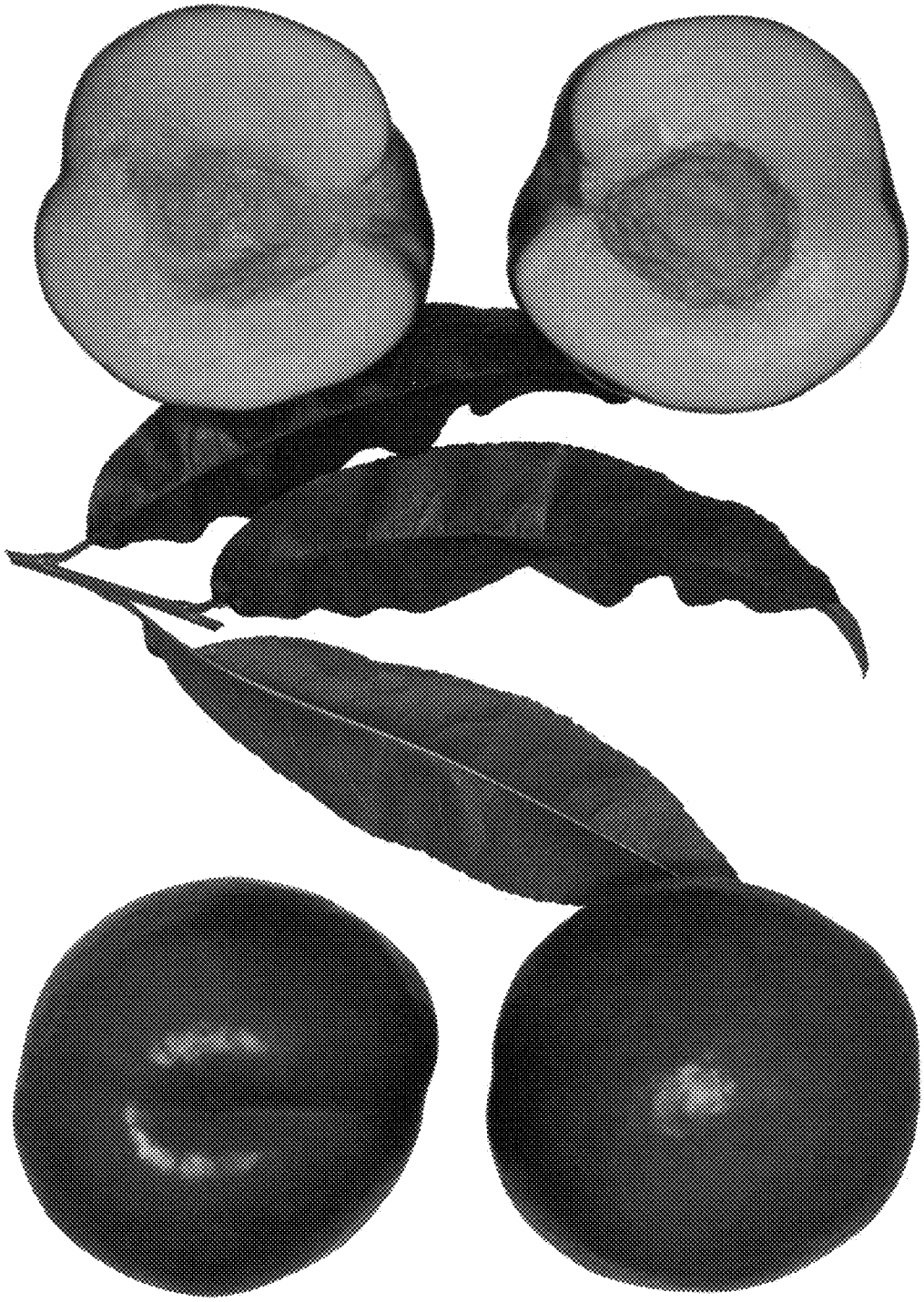

* * * * *